(12) United States Patent
Inatomi et al.

(10) Patent No.: US 7,040,804 B2
(45) Date of Patent: May 9, 2006

(54) METHOD FOR MEASURING DIFFUSION COEFFICIENT IN CONDUCTIVE MELTS, AND APPARATUS FOR MEASURING THE SAME

(75) Inventors: Yuko Inatomi, Sagamihara (JP); Kazuhiko Kuribayashi, Sagamihara (JP)

(73) Assignee: The Institute of Space and Astronautical Science, Sagamihara (JP)

( * ) Notice: Subject to any disclaimer, the term of this patent is extended or adjusted under 35 U.S.C. 154(b) by 0 days.

(21) Appl. No.: 10/608,496

(22) Filed: Jun. 30, 2003

(65) Prior Publication Data

US 2004/0118190 A1    Jun. 24, 2004

(30) Foreign Application Priority Data

Dec. 18, 2002   (JP) .............................. 2002-367056

(51) Int. Cl.
*G01N 13/00* (2006.01)
(52) U.S. Cl. ..................... 374/43; 374/137; 374/139; 374/160
(58) Field of Classification Search ............ 374/43–45, 374/137, 139, 140, 159, 160; 73/64.47; 373/150, 373/156; 164/453
See application file for complete search history.

(56) References Cited

U.S. PATENT DOCUMENTS

| 3,097,425 | A | * | 7/1963 | Name not available ..... 228/208 |
| 3,395,240 | A | * | 7/1968 | Kemeny et al. .............. 373/90 |
| 3,417,461 | A | * | 12/1968 | Wells et al. ................. 228/194 |
| 3,496,630 | A | * | 2/1970 | Velzor et al. ............... 228/194 |
| 3,575,544 | A | * | 4/1971 | Bruning ........................ 373/90 |
| 3,675,310 | A | * | 7/1972 | Schwaneke et al. ........ 228/205 |
| 3,957,194 | A | * | 5/1976 | Woodward .................. 228/194 |
| 3,993,238 | A | * | 11/1976 | Brook et al. ................ 228/198 |
| 4,034,906 | A | * | 7/1977 | Carlson et al. ............. 228/194 |
| 4,242,553 | A | * | 12/1980 | Frosch et al. ............... 117/211 |

(Continued)

FOREIGN PATENT DOCUMENTS

| CN | A 1 232 968 | 10/1999 |
| CN | A 1 299 047 | 6/2001 |

(Continued)

OTHER PUBLICATIONS

Angemeldete Teilneimer, brochure. Sep. 2002.*

(Continued)

*Primary Examiner*—Gail Verbitsky
(74) *Attorney, Agent, or Firm*—Oliff & Berridge, PLC

(57) ABSTRACT

Two conductive solid materials with their respective different compositions are joined in parallel with a gravity direction thereof, and then, heated and melted under static magnetic field orthogonal to the gravity direction to form two conductive melts with their respective different compositions. Then, the conductive melts are maintained for a predetermined period of time under the static magnetic field, and cooled and solidified.

17 Claims, 2 Drawing Sheets

U.S. PATENT DOCUMENTS

| | | | | |
|---|---|---|---|---|
| 4,263,606 A | * | 4/1981 | Yorikane | 257/737 |
| 4,333,796 A | * | 6/1982 | Flynn | 376/100 |
| 4,441,541 A | * | 4/1984 | Block | 164/453 |
| 4,679,613 A | * | 7/1987 | Chia et al. | 164/453 |
| 4,727,633 A | * | 3/1988 | Herrick | 228/124.6 |
| 4,875,617 A | * | 10/1989 | Citowsky | 228/123.1 |
| 5,451,274 A | * | 9/1995 | Gupta | 148/512 |
| 5,668,827 A | * | 9/1997 | Goy | 373/156 |
| 6,113,688 A | * | 9/2000 | Kawanishi et al. | 117/30 |
| 6,252,211 B1 | * | 6/2001 | Isoyama et al. | 219/603 |
| 6,252,402 B1 | * | 6/2001 | Sanfilippo et al. | 324/312 |
| 6,542,535 B1 | * | 4/2003 | Fishman et al. | 373/150 |
| 6,592,252 B1 | * | 7/2003 | Baba | 374/43 |

FOREIGN PATENT DOCUMENTS

| | | | |
|---|---|---|---|
| GB | 1204052 | * | 9/1970 |
| JP | 62127164 A | * | 6/1987 |
| JP | A-63-172941 | | 7/1988 |
| JP | A-11-176630 | | 7/1999 |
| JP | A-2000-294793 | | 10/2000 |
| RU | 2111085 C1 | * | 5/1998 |
| RU | 2194779 C2 | * | 12/2002 |
| RU | 2224966 C1 | * | 2/2004 |
| SU | A 1 346 977 | | 10/1987 |

OTHER PUBLICATIONS

A Method for Measuring the Interdiffusion Coefficient in a Liquid Alloy. Gonella et al. Aug. 1999.*

Thermodynamic and Kinetic Study of Phase Transformation in Solder/ Metal Systems. Cromik et al. no date.*

Inatomi et al., "Morphological Stability of GaP(1 1 1)B in LBE Under Static Magnetic Field," Journal of Crystal Growth, vol. 241, No. 4, pp. 395-403, Jun. 2002.

Takuma Miyake et al., "Measurement of Diffusion Coefficient in Liquid Metal under Static Magnetic Field," Jpn. J. Appl. Phys., vol. 41, pp. L811-L813, Part 2, No. 7A, Jul. 1, 2002.

* cited by examiner

METHOD FOR MEASURING DIFFUSION COEFFICIENT IN CONDUCTIVE MELTS, AND APPARATUS FOR MEASURING THE SAME

BACKGROUND OF THE INVENTION

1. Field of the Invention

This invention relates to a method and an apparatus for measuring diffusion coefficient in a melt, which are preferably usable in steel making, metal forging/refining or semiconductor fabricating technique.

2. Related Art

In material processing technique such as steel making, metal forging/refining or semiconductor fabricating technique, diffusion coefficient in a melt is an important parameter in order to enhance the quality of the intended material. Conventionally, however, precise measurement technique for the diffusion coefficient is not established, so that the intended material is provided by changing parameters and varying the parameters in an impromptu manner. In this point of view, therefore, with the fabricating the intended material, for example, from a melt, uniform fabricating condition has been required, in consideration of diffusion coefficient as an important parameter.

SUMMARY OF THE INVENTION

It is an object of the present invention to provide a method and an apparatus for measuring a diffusion coefficient, or more correctly, an inter-diffusion coefficient, in conductive melts precisely.

In order to achieve the above object, this invention relates to a method for measuring diffusion coefficient in conductive melts, comprising the steps of:

joining two conductive solid materials with their respective different compositions in parallel with a gravity direction thereof, heating and melting the conductive solid materials under static magnetic field orthogonal to the gravity direction to form two conductive melts with their respective different compositions therefrom, maintaining the conductive melts for a predetermined period of time under the static magnetic field, and cooling and solidifying the conductive melts.

This invention also relates to an apparatus for measuring diffusion coefficient in conductive melts, comprising:

heater for heating and melting two conductive solid materials with their respective different compositions which are joined along a gravity direction thereof, to form two conductive melts with their respective different compositions, holder for maintaining the conductive melts, and magnetic field-applying means for applying static magnetic field to the conductive melts in orthogonal to the gravity direction.

In the present invention, the two conductive solid materials are joined along the gravity direction, and static magnetic field is applied to the joined conductive solid material along a direction orthogonal to the gravity direction. Then, the joined conductive material is heated and melted, and maintained for a predetermined period of time. In the maintaining process of the joined conductive material which is melted, therefore, convection in the melt is repressed effectively by orienting the orthogonal direction and aligning the magnetic field substantially parallel to the interface of the two conductive solid materials, as shown in FIG. 2, so that the two conductive materials which are joined and melted can be diffused each other. As a result, the diffusion coefficient between the two conductive materials in the melt can be measured precisely. Herein, the "diffusion coefficient" means inter-diffusion coefficient between the two conductive materials.

In a preferred embodiment of the present invention, with the maintaining process, if the height and the width of each conductive melt from each conductive solid material is set to "h" and "w", respectively, the ratio of (w/h) is set to 1/5 or below. In this case, since the width of the conductive melt is set much smaller than the height of the conductive melt, the convection in the conductive melt can be repressed more effectively, and thus, the diffusion coefficients of the two conductive materials in the melt can be measured much precisely.

In another preferred embodiment of the present invention, the conductive melts from the two conductive solid materials are maintained in a non-conductive vessel. In this case, no thermoelectromotive force is generated between the conductive melts and the vessel, so that the convection in the conductive melts due to the thermoelectromotive force can be repressed much effectively, and thus, the diffusion coefficient between the two conductive materials in the melt can be measured much precisely.

BRIEF DESCRIPTION OF THE DRAWINGS

For better understanding of the present invention, reference is made to the attached drawings, wherein.

DESCRIPTION OF THE PREFERRED EMBODIMENTS

This invention will be described in detail with reference to the accompanying drawings.

Figure 1:
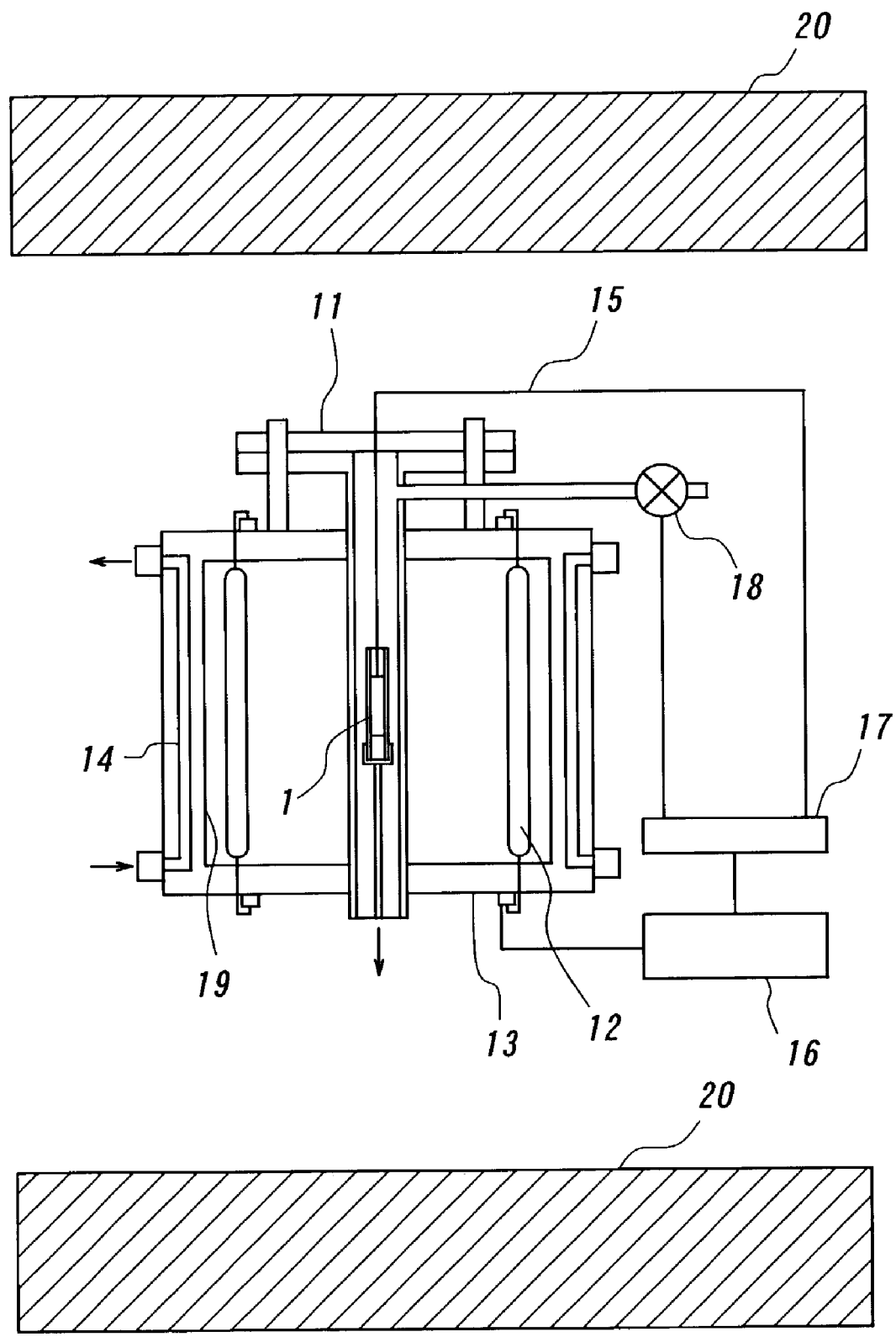
FIG. 1 is a structural view schematically showing an apparatus for measuring diffusion coefficient in conductive melts according to the present invention.
Figure 2:
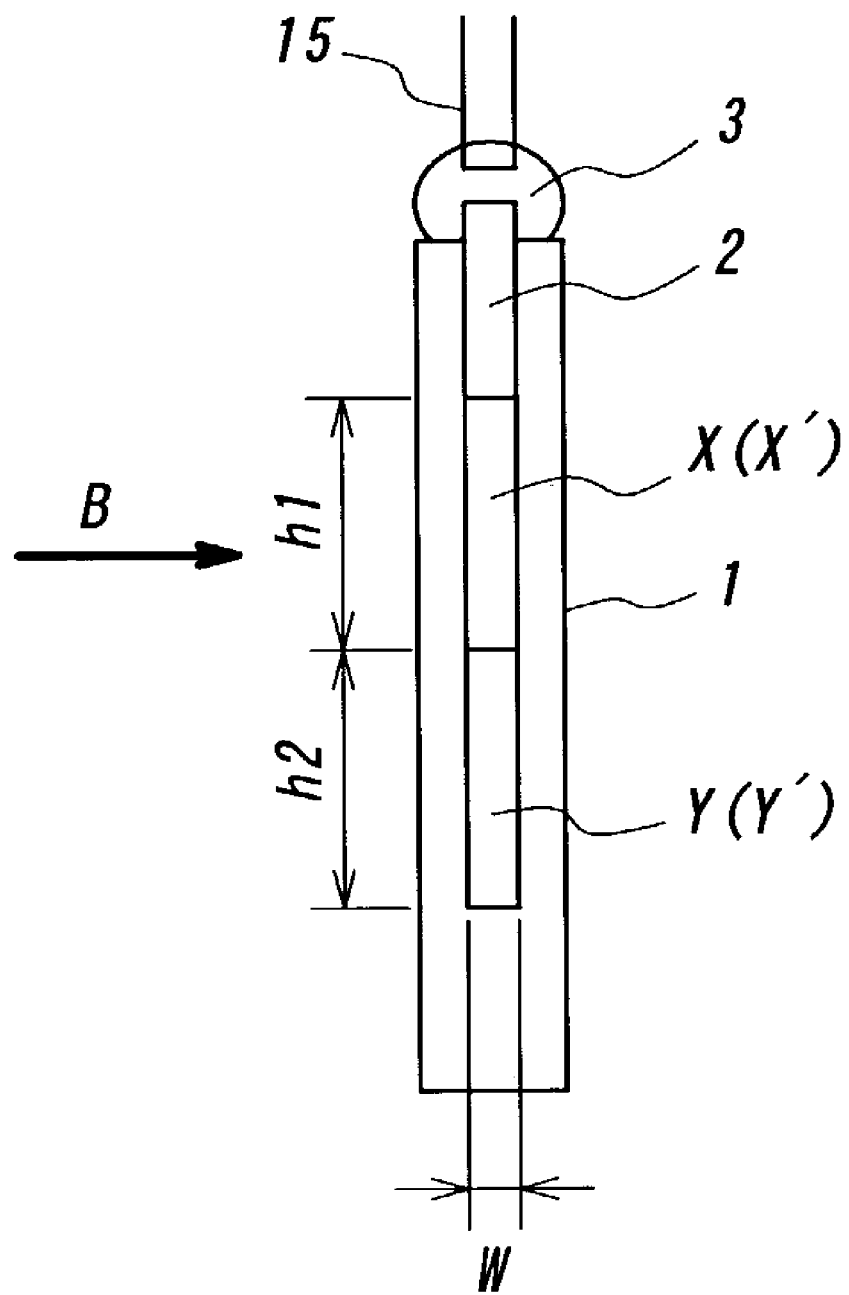
FIG. 2 is an enlarged view showing the vessel to maintain the conductive melts of the apparatus illustrated in FIG. 1.

FIG. 1 is a structural view schematically showing an apparatus for measuring diffusion coefficient in conductive melts according to the present invention, and FIG. 2 is an enlarged view showing the vessel to maintain the conductive melts of the apparatus illustrated in FIG. 1.

In the measuring apparatus of diffusion coefficient, as illustrated in FIG. 1, a reactor 11 made of quartz is disposed at the center of a furnace 13, and a halogen lamp 12 is disposed in the furnace 13 so as to enclose the reactor 11. A vessel 1 is fixed in the reactor 11 so as to be disposed at the center of the furnace 13. In the vessel 1 are charged two conductive solid materials with their respective different compositions. The reactor 11 is positioned in a cylindrical superconducting magnet 20, so that static magnetic field is applied orthogonal to the vessel 1.

To the vessel 1 is attached a thermocouple 15, whereby the interior temperature of the vessel 1 is measured via a controller 17. To the halogen lamp 12 is supplied a given electric power from an electric power supply 16, whereby the two conductive solid materials are heated by the radiation of the halogen lamp 12 and the reflection of a refection plate 19. The output of the electric power supply 16 is monitored by the controller 17 and thus, the interior space of the vessel 1 can be heated to a predetermined temperature with the temperature monitoring by the thermocouple 15. The interior space of the vessel 1 is evacuated with a vacuum pump (not shown) so that the conductive melts made of the conductive solid materials is not contaminated by impurities.

To the upper side of the reactor 11 is provided a purge line via a valve 18, whereby the reactor 11 is purged on control signal from the controller 17 after measurement of diffusion coefficient. In the side wall of the furnace 13 is built a cooling water line 14, whereby the furnace 13 is cooled and maintained within a not overheated temperature range.

In the vessel 1, as shown in FIG. 2, the conductive solid materials X and Y are charged so as to be joined along the gravity direction. The vessel 1 is sealed with a lid 2. At the top of the vessel 1 is provided a paste 3 to fix the thermocouple 15.

Next, the measuring process of diffusion coefficient using the measuring apparatus will be described. First of all, the interior space of the reactor 11 is evacuated with the vacuum pump (not shown), and static magnetic field B is applied to the conductive solid materials X and Y so as to be orthogonal to the gravity direction.

Then, electric power is supplied to the halogen lamp 12 from the electric power supply 16 to heat the vessel 1 and thus, melt the conductive solid materials X and Y. As mentioned above, since the output of the electric power supply 16 and the interior temperature of the vessel 1 are monitored and controlled by the controller 17, the heating-melting condition (temperature and time) can be controlled precisely.

The conductive melts X' and Y' made of the conductive solid materials X and Y are maintained along the gravity direction for a predetermined period of time under the static magnetic field B.

In this state, the conductive melts X' and Y' diffuse each other. As mentioned above, since the static magnetic field B is applied orthogonal to the conductive melts X' and Y' in the maintaining process, convection in the melts X' and Y' can be repressed effectively by choosing this orthogonal direction, so that the diffusion process of the melts X' and Y' can be performed precisely.

The strength of the static magnetic field B is not restricted only if the convection in the melts X' and Y' can be repressed effectively, but preferably set to 1 T or over, more preferably within 4 T–5 T. In this case, the convection in the melts X' and Y' can be repressed more effectively and the diffusion process of the melts X' and Y' can be performed more precisely.

After measurement, the conductive melts X' and Y' are cooled down to terminate the diffusion process of the melts X' and Y'. The cooling rate is preferably set to 20° C./minute or over. In this case, the diffusion process can be terminated immediately after measurement, so that the measurement error can be reduced efficiently.

The diffusion coefficient between the melts X' and Y' can be calculated on the equation of $L=(Dt)^{1/2}$ (L: diffusion length, D: diffusion coefficient, t: diffusion time (maintaining period of time of the melts)). The diffusion lengths of the melts X' and Y' is measured from the solid solution after the diffusion process.

In this embodiment, the vessel 1 is preferably made from a non conductive material. In this case, no thermoelectromotive force is generated between the conductive melts X', Y' and the vessel 1 so that the convection in the melts X' and Y' due to the thermoelectromotive force can be repressed more effectively.

The vessel 1 can be made from any non conductive material, but preferably from not expensive graphite with large mechanical strength.

As shown in FIG. 2, if the heights and the widths of the conductive melts X' and Y' in the vessel 1 are set to h1, h2 and w, respectively, the ratios of w/h1 and w/h2 are preferably set to 1/5 or below, more preferably within 1/10–1/5. In this case, since the widths of the melts X' and Y' is set much smaller than the heights (lengths) thereof, the convection in the melts X' and Y' can be repressed more effectively, so that the diffusion coefficient between the melts can be measured much precisely. If the ratio of w/h1 or w/h2 is set larger than 1/5, the diffusion coefficient between the melts X' and Y' may not be measured due to the low viscosity.

With the above-mentioned measuring method and measuring apparatus, an In-15at %Sn melt and an In-25at %Sn melt are contacted to measure the inter-diffusion coefficient thereof. The inter-diffusion coefficient measured at 900° C. was $1.1 \times 10^{-9}$ m$^2$/s, which corresponds to an inter-diffusion coefficient measured in microgravity environment Although the present invention was described in detail with reference to the above examples, this invention is not limited to the above disclosure and every kind of variation and modification may be made without departing from the scope of the present invention.

As mentioned above, according to the present invention, a method and an apparatus for measuring diffusion coefficient in conductive melts precisely can be provided.

What is claimed is:

1. A method for measuring an inter-diffusion coefficient in electrically conductive melts, comprising the steps of:

joining together two electrically conductive solid materials with their respective different compositions in parallel with a gravity direction thereof, heating and melting said electrically conductive solid materials under static magnetic field orthogonal to said gravity direction to form two electrically conductive melts with their respective different compositions therefrom, wherein an interface of the two conductive solid materials is substantially parallel to the magnetic field, maintaining said electrically conductive melts for a predetermined period of time under said static magnetic field, cooling and solidifying said conductive melts, and measuring an inter-diffusion coefficient between said conductive solid materials after cooling and solidifying said conductive melts.

2. The measuring method as defined in claim 1, wherein a ratio (w/h) is set to 1/5 or below if a height and a width of each conductive melt is set to "h" and "w", respectively.

3. The measuring method as defined in claim 1, wherein said conductive melts are maintained in a non-conductive vessel.

4. The measuring method as defined in claim 3, wherein said non-conductive vessel is made from graphite.

5. The measuring method as defined in claim 1, wherein a strength of said static magnetic field is set to 1 T or over.

6. The measuring method as defined in claim 1, wherein said conductive melts are cooled at a rate of 20°C./minute or over.

7. The measuring method as defined in claim 1, wherein at least one of said conductive melts is an In-Sn melt.

8. An apparatus for measuring inter-diffusion coefficient in electrically conductive melts, comprising:

heater for heating and melting two electrically conductive solid materials with their respective different compositions which are joined along a gravity direction thereof, to form two electrically conductive melts with their respective different compositions, holder for maintaining said electrically conductive melts, magnetic field-applying means for applying static magnetic field to said electrically conductive melts in a direction orthogonal to said gravity direction, wherein an interface of the two conductive solid materials is substantially parallel to the magnetic field, and measuring means for measuring an inter-diffusion coefficient between said conductive solid materials after cooling and solidifying said conductive melts, the inter-diffusion coefficient being a measure of mutual diffusion of said conductive melts into each other.

9. The measuring apparatus as defined in claim 8, wherein a ratio (w/h) is set to 1/5 or below if a height and a width of each conductive melt is set to "h" and "w", respectively.

10. The measuring apparatus as defined in claim 8, wherein said holder is made from a non-conductive vessel.

11. The measuring apparatus as defined in claim 10, wherein said non-conductive vessel is made from graphite.

12. The measuring apparatus as defined in claim 8, wherein a strength of said static magnetic field is set to 1 T or over.

13. The measuring apparatus as defined in claim 12, wherein said magnetic field-applying means is constructed of a superconducting magnet.

14. The measuring apparatus as defined in claim 8, wherein at least one of said conductive melts is an In-Sn melt.

15. The measuring method as defined in claim 1, wherein said inter-diffusion coefficient is calculated according to an equation $L=(Dt)^{1/2}$, wherein L is the diffusion length, D is the inter-diffusion coefficient and t is the diffusion time.

16. The measuring apparatus as defined in claim 8, wherein said inter-diffusion coefficient is calculated according to an equation $L=(Dt)^{1/2}$, wherein L is the diffusion length, D is the inter-diffusion time.

17. A method for measuring an inter-diffusion coefficient in electrically conductive melts, comprising the steps of:

joining together two electrically conductive solid materials with their respective different compositions in parallel with a gravity direction thereof, heating and melting said electrically conductive solid materials under static magnetic field orthogonal to said gravity direction to form two electrically conductive melts with their respective different compositions therefrom, wherein an interface of the two conductive solid materials is substantially parallel to the magnetic field, maintaining said electrically conductive melts for a predetermined period of time under said static magnetic field, cooling and solidifying said conductive melts, and measuring an inter-diffusion coefficient between said conductive solid materials by determining a degree of mutual diffusion of said conductive melts into each other after cooling and solidifying said conductive melts.

* * * * *